US010667796B2

(12) United States Patent
Perrey et al.

(10) Patent No.: US 10,667,796 B2
(45) Date of Patent: Jun. 2, 2020

(54) METHOD AND SYSTEM FOR REGISTERING A MEDICAL IMAGE WITH A GRAPHICAL MODEL

(71) Applicant: General Electric Company, Schenectady, NY (US)

(72) Inventors: Christian Perrey, Mondsee (AT); Arthur Gritzky, Pollham (AT)

(73) Assignee: General Electric Company, Schenectady, NY (US)

( * ) Notice: Subject to any disclaimer, the term of this patent is extended or adjusted under 35 U.S.C. 154(b) by 997 days.

(21) Appl. No.: 14/492,738

(22) Filed: Sep. 22, 2014

(65) Prior Publication Data

US 2016/0081658 A1    Mar. 24, 2016

(51) Int. Cl.
*A61B 8/00* (2006.01)
*A61B 8/08* (2006.01)
*G06T 7/30* (2017.01)

(52) U.S. Cl.
CPC .............. *A61B 8/5238* (2013.01); *G06T 7/30* (2017.01); *G06T 2207/10136* (2013.01)

(58) Field of Classification Search
CPC ........ A61B 8/5238; G06T 2207/10136; G06T 7/30
See application file for complete search history.

(56) References Cited

U.S. PATENT DOCUMENTS

| 7,466,849 | B2 | 12/2008 | Haider et al. | |
| 2007/0012880 | A1* | 1/2007 | Haider | A61B 6/00 250/363.02 |
| 2007/0280669 | A1* | 12/2007 | Karim | G03B 11/00 396/155 |
| 2011/0249876 | A1* | 10/2011 | Dewaele | G06T 3/0068 382/128 |
| 2013/0169641 | A1* | 7/2013 | Schroecker | G06T 15/08 345/426 |
| 2014/0058261 | A1* | 2/2014 | Ichioka | A61B 8/4254 600/440 |
| 2014/0108053 | A1 | 4/2014 | Akaki et al. | |

* cited by examiner

*Primary Examiner* — Ruth S Smith (57) ABSTRACT

An ultrasound imaging system and method includes accessing a graphical model of a representative patient, accessing a medical image of an anatomical structure, and registering the medical image with the graphical model to generate a composite image. The imaging system and method includes displaying the composite image and simultaneously displaying an unregistered medical image of the anatomical structure with the composite image. The unregistered medical image has at least one of a higher resolution and a larger form factor than the registered medical image.

18 Claims, 6 Drawing Sheets

METHOD AND SYSTEM FOR REGISTERING A MEDICAL IMAGE WITH A GRAPHICAL MODEL

FIELD OF THE INVENTION

This disclosure relates generally to a method and system for generating a composite image by registering a medical image of an anatomical structure with a graphical model, displaying the composite image, and simultaneously displaying an unregistered medical image of the anatomical structure with the composite image.

BACKGROUND OF THE INVENTION

In order to interpret and understand the information contained in a medical image, it is imperative that viewers of the image understand the anatomy represented in the image as well as the orientation from which the image was acquired. Properly recognizing and identifying the anatomy represented in a medical image can be difficult for many people including patients, family members of the patient, medical students and inexperienced doctors. It may be difficult to properly identify the anatomy shown in any type of medical image including computed tomography (CT) images, magnetic resonance imaging (MRI) images, x-ray images, positron emission tomography (PET) images, single photon emission computed tomography (SPECT) images, and ultrasound images. However, the problem may be especially apparent with modalities such as ultrasound where images are acquired and shared with the others either very quickly after the acquisition or in real-time. When viewing a medical image it is desirable to quickly and accurately communicate the organ/anatomy displayed in the medical image as well as the relative orientation of the organ/anatomy with respect to the patient's body in a way that is easy to interpret even for people with either limited or no formal medical training.

For these and other reasons an improved method of medical imaging and ultrasound imaging system are desired.

BRIEF DESCRIPTION OF THE INVENTION

The above-mentioned shortcomings, disadvantages and problems are addressed herein which will be understood by reading and understanding the following specification.

In an embodiment, a method of medical imaging includes accessing a graphical model of a representative patient, accessing a medical image of an anatomical structure, and registering the medical image with the graphical model to generate a composite image. The method includes displaying the composite image, and simultaneously displaying an unregistered medical image of the anatomical structure with the composite image, where the unregistered medical image has at least one of a higher resolution and a larger form factor than the registered medical image.

In an embodiment, an ultrasound imaging system includes a probe, a display device, and a processor in electronic communication with the probe and the display device. The processor is configured to access a graphical model of a representative patient, access a medical image of an anatomical structure, and register the medical image with the graphical model to generate a composite image. The processor is configured to display the composite image on the display device and simultaneously display an unregistered medical image of the anatomical structure on the display device with the composite image, where the unregistered medical image has at least one of a higher resolution and a larger form factor than the registered medical image.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
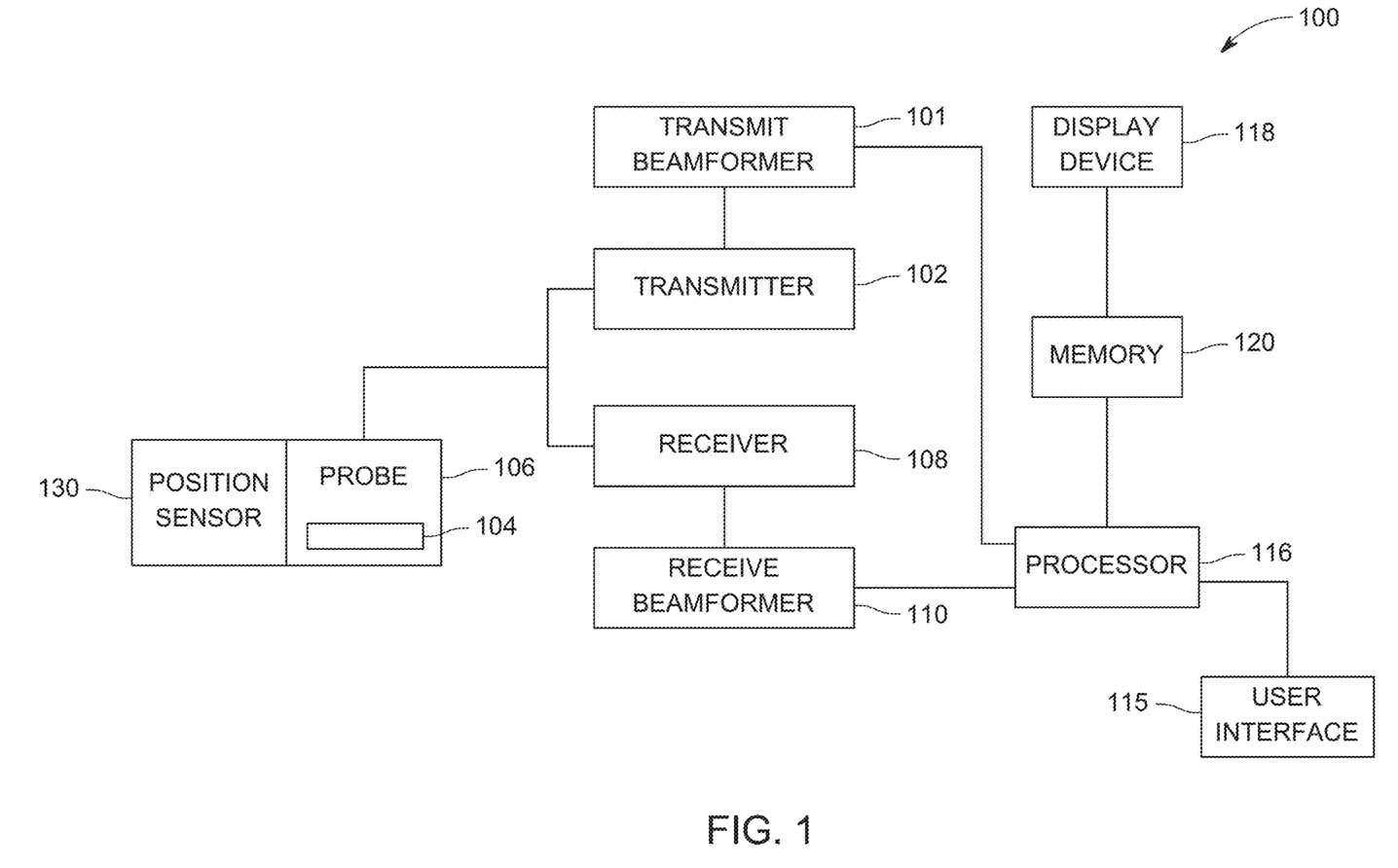
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be a linear probe, a curved linear probe, a 2D array, a mechanical 3D/4D probe, or any other type of probe capable of acquiring ultrasound data. Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes a processor 116 to control the transmit beamformer 101, the transmitter 102, the receiver 108 and the receive beamformer 110. The processor 116 is in electronic communication with the probe 106. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The display device 118 may comprise a monitor, an LED display, a cathode ray tube, a projector display, or any other type of apparatus configured for displaying an image. Additionally, the display device 118 may include one or more separate devices. For example, the display device 118 may include two or more monitors, LED displays, cathode ray tubes, projector displays, etc. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, an FPGA, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For purposes of this disclosure, the term "real-time" will be additionally defined to include an action occurring within 2 seconds. For example, if data is acquired, a real-time display of that data would occur within 2 seconds. Those skilled in the art will appreciate that most real-time procedures/processes will be performed in substantially less time than 2 seconds. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a given frame-rate or volume-rate. Images generated from the data may be refreshed at a similar frame-rate or volume-rate. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

According to some embodiments, a position sensor 130 may be attached to the probe 106 as shown in FIG. 1. The position sensor 130 may include one or more of the following: an electromagnetic sensor, an accelerometer, a gyroscopic sensor, an optical sensor, or any other type of sensor that may be used to determine the position and orientation of the probe 106. The position sensor 130 may be a component of a tracking system. The tracking system may additionally include a field generator for embodiments where the position sensor is an electromagnetic sensor or an optical tracking base unit for embodiments where the position sensor 130 is an optical sensor. It should be appreciated that embodiments may not include the position sensor 130.

Figure 2:
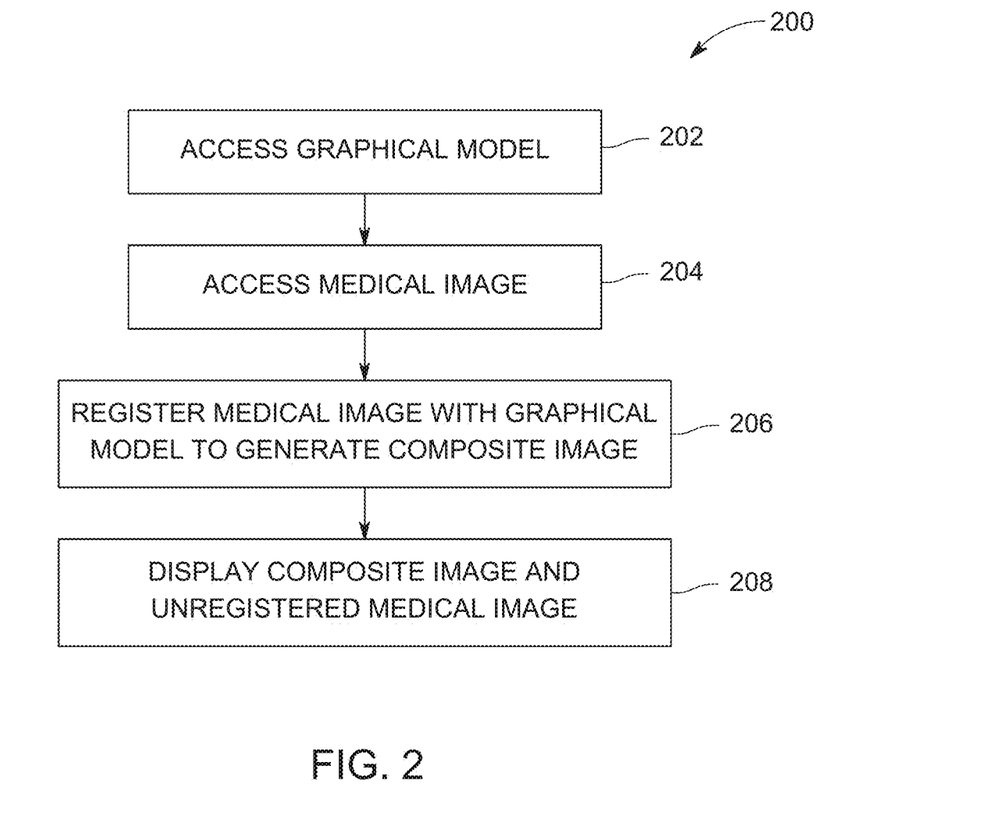
FIG. 2 is a flow chart of a method in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of a composite image and an unregistered medical image. The method 200 will be described according to an exemplary embodiment using the system of FIG. 1. However, it should be appreciated that the method 200 may be performed with other types of medical imaging systems including a CT imaging system, a PET imaging system, an MR imaging system, a SPECT imaging system, an X-ray imaging system, or any other type of medical imaging system. Additionally, the method 200 may be performed by a processor in a workstation or a PC that is separate from the medical imaging system used to acquire the medical images.

For example, a processor may access the medical images and the graphical model from a database, over a network, or from one or more medical imaging systems.

Figure 3:
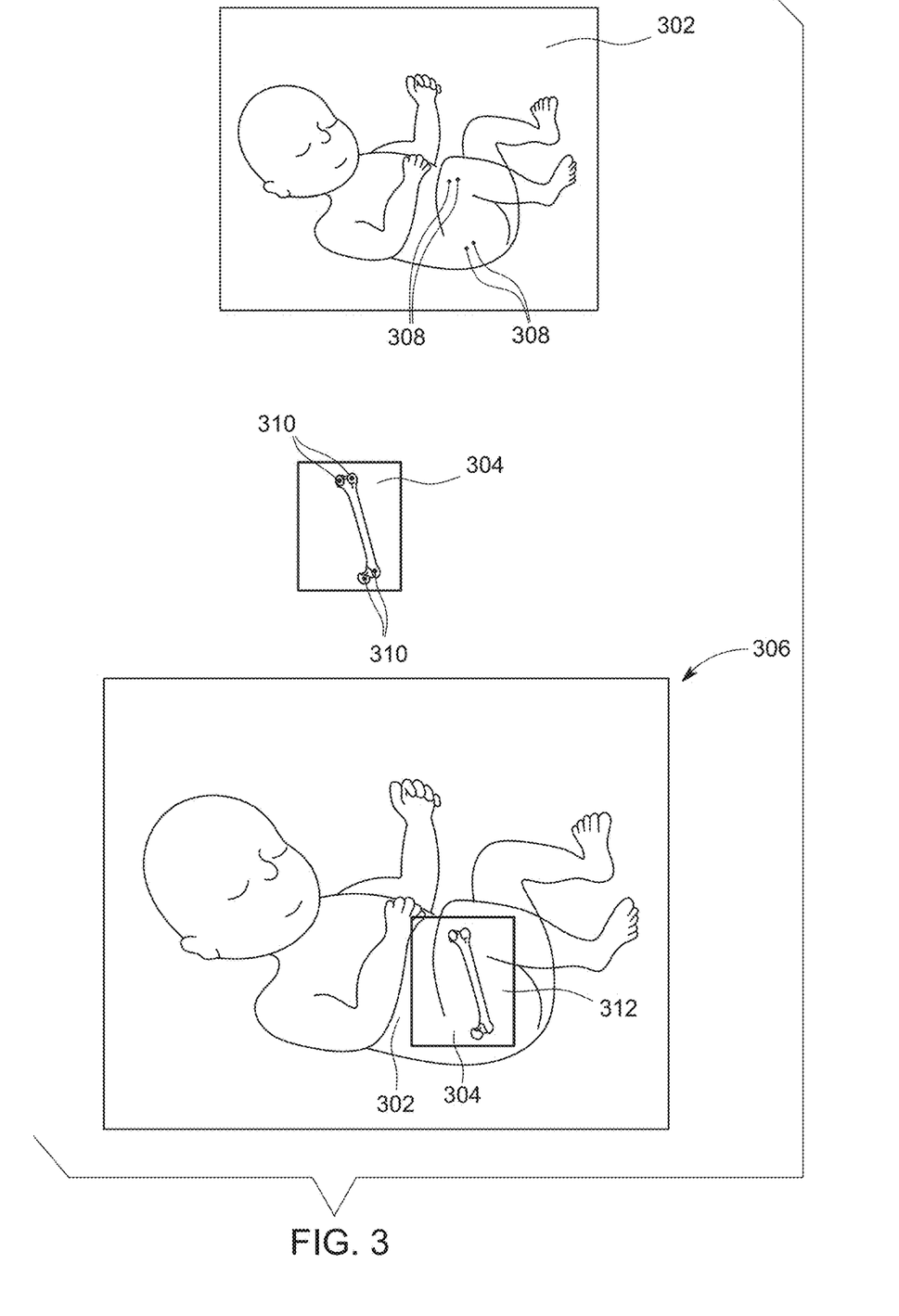
FIG. 3 is a schematic representation of the steps performed during the generation of a composite image according to an exemplary embodiment.

FIG. 3 is a schematic representation of the steps performed during the generation of a composite image according to an exemplary embodiment. FIG. 3 includes a 3D graphical model 302, a medical image 304, and a composite image 306. FIG. 3 will be described in additional detail with respect to the method 200.

Referring to FIG. 2, at step 202, the processor 116 accesses a graphical model from a memory such as the memory 120. The graphical model is a model of a representative patient. The graphical model may include a 3D graphical model, such as the 3D graphical model 302 shown in FIG. 3 or a 2D graphical model. The 3D graphical model 302 includes information of the representative patient in three dimensions including a depth direction. The 2D graphical model may be a 2D representation of a representative patient that does not include any information in a depth direction. An example of a 2D graphical model will be described hereinafter. According to an exemplary embodiment, the 3D graphical model 302 may be displayed as a rendering, similar to a volume-rendered image commonly shown in diagnostic imaging, or a different type of 3D representation.

According to various embodiments, the graphical model may range anywhere from extremely life-like to a very abstract model of a representative patient. For example, the graphical model 302 may be based on a statistically average or representative patient. According to other embodiments, the graphical model may be less life-like. For example, in some embodiments, the graphical model may be a stick model, a block or polygon model, a cartoon-based representation, or any other type of representation.

Next, at step 204, the processor 116 accesses a medical image, such as the medical image 304. The processor 116 may access the medical image 304 from a memory, such as the memory 120 or from a database or server (not shown). According to another embodiment, accessing the medical image 304 may include accessing the medical image 304 from a remote memory or database such as a picture archiving and communication system (PACS). The medical image may include either a 2D medical image or a 3D medical image according to various embodiments. Additionally, for modalities like ultrasound and CT, a medical image may include many different image frames acquired from different spatial locations, and/or the medical image may include many different image frames acquired at different times, such as a cine loop. Accessing the medical image may also include acquiring medical image data with an medical imaging system.

At step 206, the processor 116 registers the medical image 304 with the 3D graphical model 302 to generate a composite image, such as the composite image 306. For purposes of this disclosure, the term "registered medical image" may be used to refer to the medical image that is registered with a graphical model to generate a composite image. The composite image 306 includes the medical image 304 overlaid or superimposed on the 3D graphical model 302. The processor 116 may register the medical image 304 with the 3D graphical model 302 according to various different techniques. The techniques may be manual, automatic, or semi-automatic. The processor 116 may register the medical image 304 to the 3D graphical model 302 based on image processing techniques. For example, if the 3D graphical model 302 is detailed enough, the processor 116 may register the medical image 304 with the 3D graphical model 302 by performing a best-fit algorithm between the 3D graphical model 302 and the medical image 304. According to other embodiments, the operator may manually register the medical image 304 with the 3D graphical model 302. For example, the operator may manually position the medical image 304 on the anatomically appropriate location of the 3D graphical model 302 based on the operator's knowledge of the patient's anatomy. Or, the operator may manually identify a number of landmarks or registration points, such as points 308 and points 310 shown in the 3D graphical model 302 and the medical image 304 respectively. According to another embodiment, the medical image 304 may be registered with the 3D graphical model based on position data acquired with a position sensor, such as the position sensor 130. The operator, may for instance, identify several corresponding points in the 3D graphical model 302 and the on the patient. According to an exemplary workflow, the operator may position the probe 106 with the position sensor 130 at a number of locations on the patient and click on corresponding locations in the 3D graphical model 302. The locations used may depend on anatomical structure represented in the medical image 304, as well as the scale of the medical image 304. During step 206, the processor 116 may adjust the graphical model for scale and/or orientation in order to better match the size and shape of the anatomy represented in the medical image 304. For example, the 3D graphical model 302 may be rotated in 3 dimensions and adjusted for sale to best match the orientation of the anatomy in the medical image 304.

The composite image 306 includes the medical image 304 overlaid on the 3D graphical model 302. The composite image 306 includes an area of overlap 312 between the medical image 304 and the 3D graphical model 302. The area of overlap 312 is the area or region of the composite image 306 where the medical image 304 and the 3D graphical model both contribute information for the composite image 306. According to an embodiment, generating the composite image 306 may include blending the medical image 304 and the 3D graphical model 302 in the area of overlap 312. For example, the composite image may show some or all of the medical image 304 and the 3D graphical model 302 in the area of overlap 312. According to other embodiments, the medical image 304 may replace the 3D graphical model 302 in the area of overlap 312 of the composite image 306. According to yet other embodiments, the operator may be able to selectively control the blending between the 3D graphical model 302 and the medical image 304 in the composite image 306. While the composite image 306 shown in FIG. 3 is generated based on a 3D graphical model, it should be appreciated that composite images may be generated based on other types of graphical models, such as a 2D graphical model in other embodiments.

Figure 4:
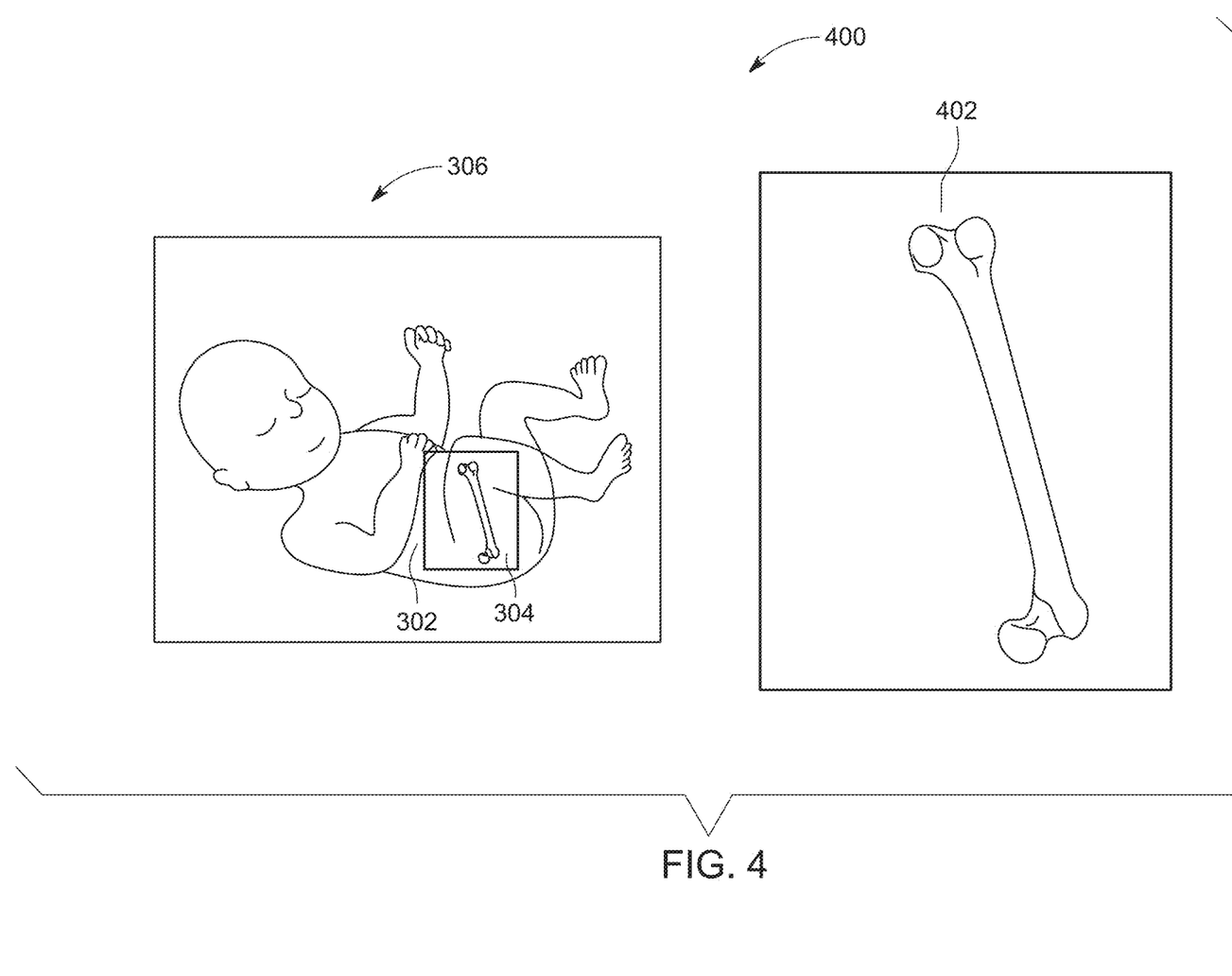
FIG. 4 is a schematic representation of a screenshot in accordance with an exemplary embodiment.

FIG. 4 is a schematic representation of a screenshot 400 according to an exemplary embodiment. The screenshot 400 includes the composite image 306, previously described with respect to FIG. 3, and an unregistered medical image 402.

At step 208 of the method 200 shown in FIG. 2, the processor 116 simultaneously displays the composite image 306 and the unregistered medical image 402. The unregistered medical image 402 may be, according to an embodiment, based on the same data as the medical image 304. According to an embodiment, the unregistered medical image 402 may be a version of the medical image 304 that has at least one of a higher resolution and a larger form factor than the medical image 304. The term "form factor" refers to the physical size of the image on the display device.

Displaying the unregistered medical image 402 with a larger form factor means that the area of the display occupied by the unregistered medical image 402 is greater than the area of the display occupied by the medical image 304. The larger form factor makes it easier for a user to examine small details in the unregistered medical image 402 compared to the medical image 304. The unregistered medical image 402 may be at least one of a higher resolution and a larger form factor than the registered medical image 304. The unregistered medical image 402 provides at least one of a higher resolution and a larger form factor to enhance the visibility of details of the anatomical structure of the patient. As previously described, the composite image 306 is generated based on the medical image 304 that represents a specific anatomical structure. The same anatomical structure is represented in the unregistered medical image 402, albeit at a higher resolution and/or with a larger form factor. According to an exemplary embodiment, the medical image 304 and the unregistered medical image 402 may both represent the same anatomical structure and the anatomical structure may be in the same relative orientations in the medical image 304 and the unregistered medical image 402. According to some embodiments, the medical image 304 may correspond to the unregistered medical image 402. This means that the unregistered medical image 402 may be a larger and/or higher resolution version of the medical image 304. This is advantageous because it would make it easier for users to understand the anatomy represented in the unregistered medical image 402 based on the medical image 304 registered to the 3D graphical model 302 as part of the composite image 306.

Displaying both the composite image 306 and the unregistered medical image 402 allows for the easier communication of images obtained through a diagnostic imaging procedure. Since the composite image 306 includes the medical image 304 registered to the 3D graphical model 302, it provides a doctor, specialist, or clinician with an easy way communicate the location of the anatomy shown in the unregistered medical image 402. Additionally, it is envisioned that the unregistered medical image 402 is either of higher resolution and/or larger form factor than the medical image 304. As such, the unregistered medical image 402 allows the doctor, specialist, or clinician an easy way to show specific details in the unregistered medical image 402 when communicating with patients or other interested parties, such as family members. The composite image 306 may be used to quickly and accurately show where the anatomical structure represented in the unregistered medical image 402 is located with respect to the 3D graphical model 302.

For real-time imaging modalities, such as ultrasound, it may be desirable to register the medical image with the graphical model, display the composite image, and simultaneously display the unregistered image all in real-time as the medical image is acquired. This means that the composite image 306 may be updated in real-time to show the location with respect to the graphical model 302 from which the medical image 304 was acquired. This is particularly helpful for use with ultrasound since clinicians routinely show patients and family members images acquired in real-time while scanning the patient. According to an exemplary embodiment, the medical image 304 and the unregistered medical image 402 may both be generated based on the same data. Additionally, according to an embodiment, the medical image 304 and the unregistered medical image 402 may both be live images that update in a synchronized manner as additional data is acquired so that both the medical image 304 and the unregistered medical image 402 show image data acquired from the same time when displaying a live image or a cine image. Additionally, only one of the medical image 304 and the unregistered medical image 402 may be a live image or a cine image, while the other of the medical image 304 and the unregistered medical image may be a still image.

Figure 5:
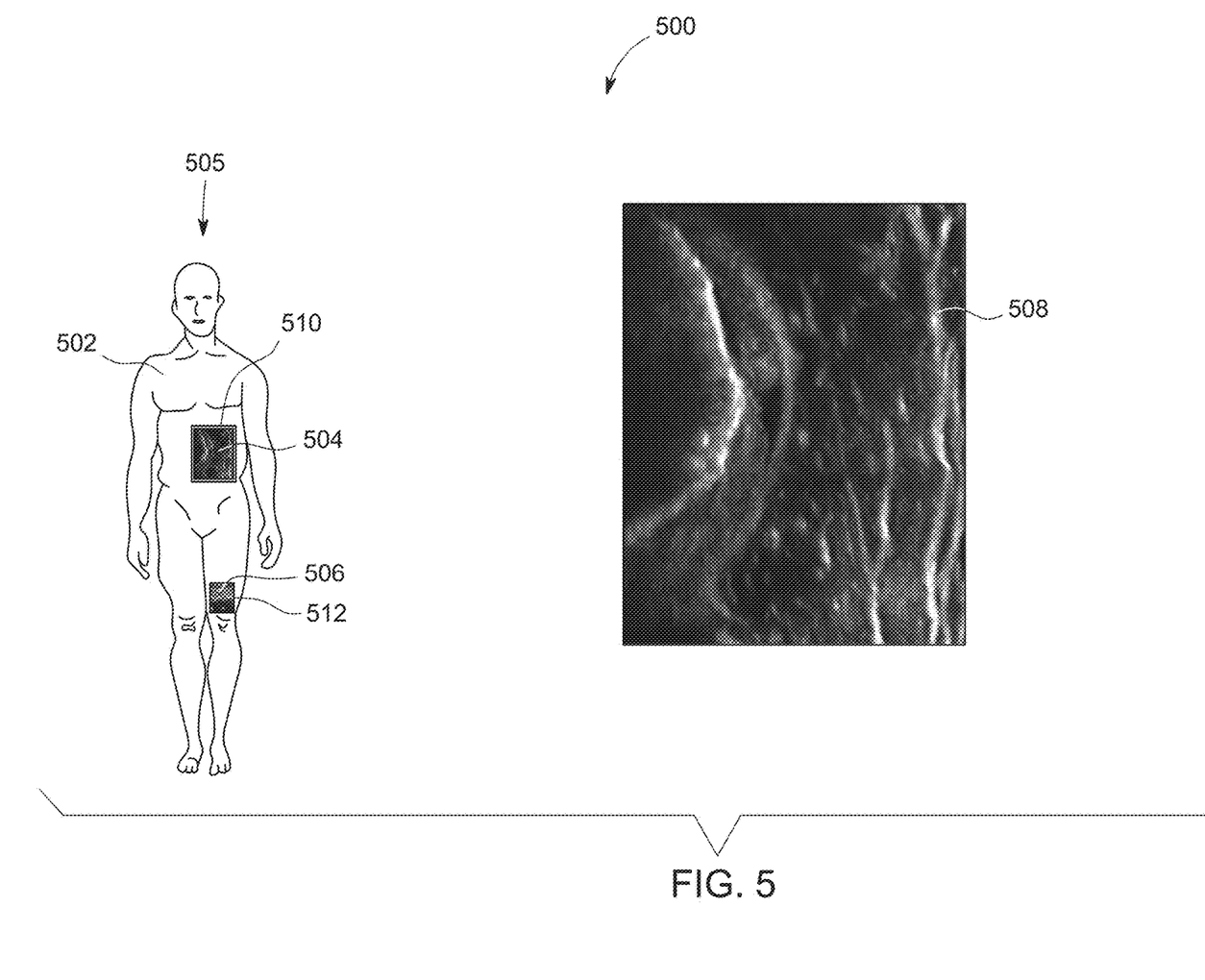
FIG. 5 is a schematic representation of a screenshot in accordance with an exemplary embodiment.

FIG. 5 is a schematic representation of a screenshot 500 according to an exemplary embodiment. The screenshot 500 includes a composite image 505 and an unregistered medical image 508. The composite image 505 is based on a 2D graphical model 502, a first medical image 504, and a second medical image 506.

According to the embodiment shown in FIG. 5, the graphical model comprises the 2D graphical model 502. The 2D graphical model 502 does not include any depth information. The composite image 505 is generated based on the 2D graphical model 502, the first medical image 504, and the second medical image 506. The first medical image 504 and the second medical image 506 are registered to the 2D graphical model 502 to generate the composite image 505. The first medical image 504 and the second medical image 506 may both represent different anatomical structures according to an embodiment. The first medical image 504 and the second medical image 506 may both be 2D images. According to other embodiments, one or both of the first medical image 504 and the second medical image 506 may be a 3D image, such as a volume-rendered image. Other embodiments may include composite images with more than two images registered to a graphical model. Composite images with more than two images registered to the graphical model may also be generated based on a 3D graphical model according to additional embodiments. The first medical image 504 and the second medical image 506 may be registered to the 2D graphical model 502 using any of the techniques that were previously described with respect to FIGS. 2, 3, and 4.

The composite image 505 may be used as part of a user interface according to an exemplary embodiment. For example, the user may use the composite image 505 to select the image displayed as the unregistered medical image 508. According to one workflow, the user may select one of a plurality of medical images displayed with the 2D graphical model 502. For example, the user may select between the first medical image 504 showing a first anatomical structure, and the second medical image 506 showing a second anatomical structure. The user may select the medical image through any method, such as selecting it with a cursor that is moved with a mouse, touch pad, trackball or any other user input device. According to one workflow, the image displayed as the unregistered medical image 508 may be a larger and/or higher resolution version of the selected medical image. If the first medical image 504 is selected, the unregistered medical image 508 will be an unregistered version of the first medical image 504. If the user selects the other medical image in the composite image 505, then the processor 116 may update the unregistered image to correspond with the most recently selected medical image. If the second medical image 506 is selected, the unregistered medical image 508 will be an unregistered version of the second medical image 506. Likewise, users could use the composite image 505 to select the image displayed as the unregistered medical image 508 for embodiments where the composite image is based on more than two medical images. According to various embodiments, the composite image 505 may be used as a user interface device allowing the user to easily select the image displayed as the unregistered medical image 508. The selected one of the medical images on the composite image 505 may be highlighted, such as by changing a color or a highlighting of the selected medical image, changing a boarder around the selected medical image, changing a color of a border around the selected medical image or any other visual technique to differentiate the selected medical image from the one or more medical images that are not selected in the composite image 505. According to an exemplary embodiment a first border 510 around the first medical image 504 is shown in bold, whereas a second border 512 around the second medical image 506 is not in bold. According to the screenshot 500, since the first medical image 504 is shown with the border 510 in bold, the unregistered medical image 508 may be version of the first medical image 504 with a larger form factor and a higher resolution.

Figure 6:
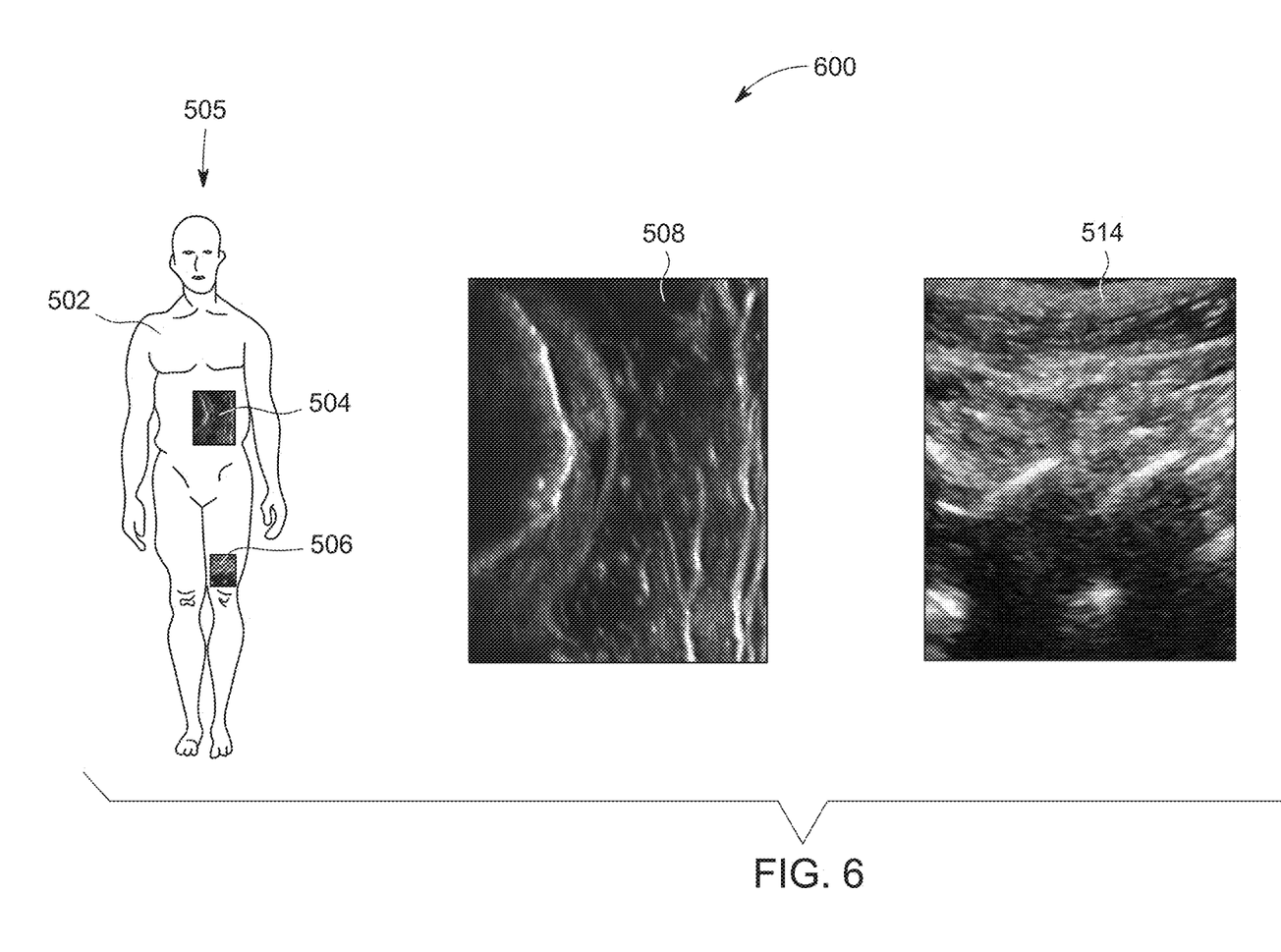
FIG. 6 is a schematic representation of a screenshot in accordance with an exemplary embodiment.

FIG. 6 is a schematic representation of a screenshot 600 according to an exemplary embodiment. The screenshot 600 includes the composite image 505, the unregistered medical image 508, and a second unregistered medical image 514. Second unregistered medical image 514 is a larger and/or higher resolution version of the second medical image 506. Common reference numbers will be used between FIGS. 5 and 6 to identify identical elements or components. The composite image 505 includes 2D graphical model 502, first medical image 504, and second medical image 506. However, instead of only displaying one unregistered medical image, the screenshot 600 includes two unregistered medical images: unregistered medical image 508 and the second unregistered medical image 514. It should be appreciated by those skilled in the art that other embodiments may display more than two unregistered medical images at the same time as the composite image 505.

According to other embodiments, multiple images may be displayed along with the composite image 505. For example, a first unregistered image based on the first medical image 504 and a second unregistered image based on the second medical image 506 may both be displayed at the same time along with the composite image 505.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of medical imaging comprising:
accessing medical image data acquired with a medical imaging system;
accessing a graphical model of a representative patient;
generating a medical image of an anatomical structure based on the medical image data;
registering the medical image with the graphical model to generate a composite image, wherein generating the composite image comprises blending the medical image and the graphical model in a region of overlap in the composite image, wherein both the medical image and the graphical model contribute to the composite image in the region of overlap, and wherein the medical image is registered in an anatomically appropriate location on the graphical model;
displaying the composite image; and
displaying an unregistered medical image of the anatomical structure at the same time as the composite image, where the unregistered medical image is based on the same medical image data as the medical image and where the unregistered medical image is at least one of a larger version of the medical image and a higher resolution version of the medical image.

2. The method of claim 1, wherein registering the medical image with the graphical model, displaying the composite image, and displaying the unregistered medical image of the anatomic structure are performed in real-time while in the process of acquiring the medical image data.

3. The method of claim 1, further comprising accessing a second medical image that is different from the medical image, and wherein generating the composite image further comprises registering the second medical image to the graphical model, where the second medical image is registered in an anatomically appropriate location with respect to the graphical model.

4. The method of claim 3, further comprising selecting the second medical image on the composite image and updating the unregistered image to correspond with the second medical image.

5. The method of claim 1, wherein the graphical model comprises a 2D graphical model.

6. The method of claim 1, wherein the graphical model comprises a 3D graphical model.

7. The method of claim 6, wherein the medical image comprises a 2D image.

8. The method of claim 6, wherein the medical image comprises a volume-rendered image.

9. The method of claim 1, further comprising selectively controlling the blending between the graphical model and the medical image in the region of overlap in the composite image.

10. An ultrasound imaging system comprising:
a probe;
a display device; and
a processor in electronic communication with the probe and the display device, wherein the processor is configured to:
control the probe to acquire ultrasound data;
access a graphical model of a representative patient;
generate a medical image of an anatomical structure based on the ultrasound data;
register the medical image with the graphical model to generate a composite image, wherein the processor is configured to generate the composite image by blending the medical image and the graphical model in a region of overlap in the composite image, wherein both the medical image and the graphical model contribute to the composite image in the region of overlap, and wherein the medical image is registered in an anatomically appropriate location on the graphical model;
display the composite image on the display device; and
display an unregistered medical image of the anatomical structure on the display device at the same time as the composite image, where the unregistered medical image is based on the same ultrasound data as the medical image and where the unregistered medical image is at least one of a larger version of the medical image and a higher resolution version of the medical image.

11. The ultrasound imaging system of claim 10, further comprising a position sensor attached to the probe, and wherein the processor is further configured to use position data from the position sensor to register the medical image with the graphical model.

12. The ultrasound imaging system of claim 10, wherein the processor is configured to automatically generate the composite image, display the composite image, and display the unregistered medical image in real-time while acquiring the ultrasound data with the probe.

13. The ultrasound imaging system of claim 10, wherein the processor is configured to generate the composite image by registering a second medical image to the graphical model, where the second medical image is different from the medical image, and where the second medical image is registered to the graphical model in an anatomically appropriate location with respect to the graphical model.

14. The ultrasound imaging system of claim 13, wherein the processor is configured to update the unregistered image to correspond with the second medical image in response to receiving a user input selecting the second medical image in the composite image.

15. The ultrasound imaging system of claim 13, wherein the medical image comprises a 2D image and the second medical image comprises a volume-rendered image.

16. The ultrasound imaging system of claim 15, wherein the graphical model comprises a 3D graphical model.

17. The ultrasound imaging system of claim 15, wherein the graphical model comprises a 2D graphical model.

18. The ultrasound imaging system of claim 10, wherein the processor is further configured to receive inputs to selectively control the blending between the graphical model and the medical image in the region of overlap in the composite image.

* * * * *